US007897574B2

(12) United States Patent
Petzelbauer et al.

(10) Patent No.: US 7,897,574 B2
(45) Date of Patent: Mar. 1, 2011

(54) PHARMACEUTICAL COMPOSITION FOR TREATING HAEMORRHAGIC SHOCK AND ITS CONSECUTIVE SYMPTOMS

(75) Inventors: Peter Petzelbauer, Vienna (AT); Rainer Henning, Uetliburg (CH)

(73) Assignee: Ikaria Development Subsidiary Two LLC, Clinton, NJ (US)

( * ) Notice: Subject to any disclaimer, the term of this patent is extended or adjusted under 35 U.S.C. 154(b) by 419 days.

(21) Appl. No.: 12/158,670

(22) PCT Filed: Nov. 10, 2006

(86) PCT No.: PCT/AT2006/000465

§ 371 (c)(1),
(2), (4) Date: Sep. 5, 2008

(87) PCT Pub. No.: WO2007/070899

PCT Pub. Date: Jun. 28, 2007

(65) Prior Publication Data

US 2009/0005310 A1 Jan. 1, 2009

(30) Foreign Application Priority Data

Dec. 23, 2005  (AT)  .............................. A 2067/2005

(51) Int. Cl.
*A61K 38/36* (2006.01)
(52) U.S. Cl. .................... 514/13.6; 514/21.3
(58) Field of Classification Search ........................ None
See application file for complete search history.

(56) References Cited

U.S. PATENT DOCUMENTS

| 5,997,844 | A | 12/1999 | Dean et al. |
| 7,271,144 | B2 | 9/2007 | Petzelbauer et al. |

FOREIGN PATENT DOCUMENTS

| AT | 414097 | 12/2005 |
| CA | 2544676 | 1/2006 |
| WO | WO-02/48180 | 6/2002 |
| WO | WO-2005/086578 | 9/2005 |
| WO | WO-2006/000007 | 1/2006 |

OTHER PUBLICATIONS

Petzelbauer, P. et al., "The fibrin-derived peptide Bbeta15-42 protects the myocardium against ischemia-reperfusion injury", *Nature Medicine*, Nature Pubkishing Group, New York, NY, US, vol. 11, No. 3, Mar. 2005, pp. 298-304.
Ledgerwood, Anna M. et al. "A review of studies on the effects of hemorrhagic shock and resuscitation on the coagulation profile." *Journal of Trauma Injury Infection and Critical Care*, vol. 54, No. 5 Supplement, Mar. 2003, pp. S68-S74.
Lee, M. E. et al. "Fragment E derived from both fibrin and fibrinogen stimulates interleukin-6 production in rat peritoneal macrophages." *Molecules and Cells*, Feb. 1999, vol. 9, No. 1, pp. 7-13.
Staton, C. A. et al. "The role of fibrinogen and related fragments in tumour angiogenesis and metastatis" *Expert Opinion on Biologial Therapy*, United Kingdom, 2003, vol. 3, No. 7, pp. 1105-1120.
Petzelbauer, P. et al., "The fibrin-derived peptide Bbeta15-42 protects the myocardium against ischemia-reperfusion injury", *Nature Medicine*, Nature Pubkishing Group, New York, NY, US, vol. 11, No. 3, Mar. 2005, pp. 298-304.
Ledgerwood, Anna M. et al. "A review of studies on the effects of hemorrhagic shock and resuscitation on the coagulation profile." *Journal of Trauma Injury Infection and Critical Care*, vol. 54, No. 5 Supplement, Mar. 2003, pp. S68-S74.
Lee, M. E. et al. "Fragment E derived from both fibrin and fibrinogen stimulates interleukin-6 production in rat peritoneal macrophages." *Molecules and Cells*, Feb. 1999, vol. 9, No. 1, pp. 7-13.
Staton, C. A. et al. "The role of fibrinogen and related fragments in tumour angiogenesis and metastatis" *Expert Opinion on Biological Therapy*, United Kingdom, 2003, vol. 3, No. 7, pp. 1105-1120.
Altieri, D. C., "Regulation of Leukocyte-Endothelium Interaction by Fibrinogen", Thrombosis and Haemostasis, 1999, vol. 82, pp. 781-786.
Herrick, S. et al., Int. J. Biochem. Cell Biol., Jul. 1999, vol. 31, No. 7, pp. 741-746, Abstract.
Loike, John D. et al., "CD11c/CD18 on neutrophils recognizes a domain at the N terminus of the Aœ chain of fibrinogen", Proc. Natl. Acad. Sci., USA, Feb. 1991, vol. 88, pp. 1044-1048.
Van Gorp, Eric C. M. et al., "Impaired Fibrinolysis in the Pathogenesis of Dengue Hemorrhagic Fever", Journal of Medical Virology, 2002, vol. 67, pp. 549-554.
Mairuhu et al., "Is clinical outcome of dengue-virus infections influenced by coagulation and fibrinolysis? A critical review of the evidence", Lancet Infect. Dis., Jan. 2003, vol. 3, No. 1, pp. 33-41, Abstract.
Idell S., "Adult respiratory distress syndrome: do selective anticoagulants help?", Am. J. Respir. Med., 2002, vol. 1, No. 6, pp. 383-391, Abstract.
Bach, et al., "VE-Cadherin mediates endothelial cell capillary tube formation in firbrin and collagen gels", Exp. Cell Res., Feb. 1998, vol. 238, No. 2, pp. 324-334, Abstract.
Chalupowicz, Diana G. et al., "Fibrin II induces endothelial cell capillary tube formation", The Journal of Cell Biology, Jul. 1995, vol. 130, No. 1, pp. 207-215.
Hamaguchi, M. et al., "Spreading of platelets on fibrin is mediated by the amino terminus of the beta chain including peptide beta 15-42", Blood, May 1, 1996, vol. 81, No. 9, pp. 2348-2356, Abstract.
Francis et al., "Endotheial cell responses to fibrin mediated by FPB cleavage and the amino terminus of the beta chain", Blood Cells, 1993, vol. 19, No. 2, pp. 291-306, Abstract.

(Continued)

*Primary Examiner*—Christina Bradley
(74) *Attorney, Agent, or Firm*—Hoffmann & Baron, LLP

(57) ABSTRACT

The invention is concerned with the use of a peptide comprising the N-terminal sequence
Gly-His-Arg-Pro-Leu-Asp-Lys-Lys-Arg-Glu-Glu-Ala-Pro-Ser-Leu-Arg-Pro-Ala-  Pro-Pro-Pro-Ile-Ser-Gly-Gly-Gly-Tyr-Arg (SEQ ID NO: 1)
or any allelic variant or derivative of said peptide possessing the biological property of matching the inducible VE-cadherin binding motif on the Bβ-chain (i.e. Bβ15-42) of human fibrin for the preparation of a pharmaceutical preparation for the treatment of shock, more specifically of hemorrhagic shock.

4 Claims, No Drawings

OTHER PUBLICATIONS

Sporn et al., "Cell proliferation on fibrin: modulation by fibrinopeptide cleavage", Blood, Sep. 1, 1995, vol. 86, No. 5, pp. 1802-1810, Absract.

Ribes, Jule A. et al., "Fibrin induces release of von Willebrand factor from endothelial cells", J. Clin. Invest., Jan. 1987, vol. 79, pp. 117-123.

Ribes, Julie A. et al., "Mediation of fibrin-induced release of von Willebrand factor from cultured endothelial cells by the fibrin β chain", J. Clin. Invest., Aug. 1989, vol. 84, pp. 435-442.

Erban et al., "A 130-kDa protein on endothelial cells binds to amino acids 15-42 of the B beta chain of fibrinogen", J. Biol. Chem., Feb. 1992, vol. 267, No. 4, pp. 2451-2458, Abstract.

Harley, Suzanne L. et al., "Regulation by fibrinogen and its products of intercellular adhesion molecule-1 expression in human saphenous vein endothelial cells", Arteriosclerosis, Thrombosis, and Vascular Biology, 2000, vol. 20, pp. 650-658.

Bach, Tami J. et al., "Endothelial cell VE-cadherin function as a receptor for the β 15-42 sequence of fibrin", J. Biol. Chem., Nov. 1998, vol. 273, No. 46, pp. 30719-30728.

Gorlatov, Sergei et al., "Interaction of fibrin(ogen) with the endothelial cell receptor VE-cadherin: Mapping of the receptor-binding site in the $NH^2$-terminal portion sof the fibrin β chains", Biochemistry, 2002, vol. 41, No. 12, pp. 4107-4116, Abstract.

Fareed et al., "Useful laboratory tests for studying thrombogenesis in acute cariac syndromes", Clin. Chem., Aug. 1998, vol. 44, No. 8, pp. 1845-1853, Abstract.

Bruce et al., "Endothelial cell spreading on fibrin requires fibrinopeptide B cleavage and amino acid residues 15-42 of the beta chain", J. Clin Invest., vol. 89, pp. 842-850. (1992).

Qi et al., "Fibrin Regulation of Interleukin-8 Gene Expression in Human Vasular Endothelial Cells", Blood, vol. 90, pp. 3593-3602, (1997).

Martinez et al. "Interaction of fibrin with VE-cadherin", Ann NY Acad Sci., vol. 936, pp. 386-405, (2001).

Ikematsu, S. "Radioimmunoassy of fibronopeptide", Rinsho kensa, 28, pp. 20-24, (1984), (CAS Abstract 100:188169).

SEQUENCE LISTING

```
<160> NUMBER OF SEQ ID NOS: 1

<210> SEQ ID NO 1
<211> LENGTH: 28
<212> TYPE: PRT
<213> ORGANISM: Homo sapiens

<400> SEQUENCE: 1

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg
            20                  25
```

PHARMACEUTICAL COMPOSITION FOR TREATING HAEMORRHAGIC SHOCK AND ITS CONSECUTIVE SYMPTOMS

This Application is the National Phase Under 35 U.S.C. §371 of PCT International Application No. PCT/AT2006/000465 which has an International filing date of Nov. 10, 2006, which claims priority to Austrian Application No. A2067/2005 filed on Dec. 23, 2005. The entire contents of all applications listed above are hereby incorporated by reference.

BACKGROUND OF THE INVENTION

The present invention is directed to a pharmaceutical preparation for the treatment of hemorrhagic shock and the sequels thereof.

Shock is an acute complication of many different pathological conditions characterized by the inability of the cardiovascular system to maintain an adequate perfusion pressure. More specifically, in hemorrhagic shock, blood loss exceeds the body's ability to compensate and provide adequate tissue perfusion and oxygenation. This frequently is due to trauma, but it may be caused by spontaneous hemorrhage (eg, GI bleeding, childbirth), surgery, and other causes.

Most frequently, clinical hemorrhagic shock is caused by an acute bleeding episode with a discrete precipitating event. Less commonly, hemorrhagic shock may be seen in chronic conditions with subacute blood loss. This condition is the leading cause of death in the age group of 1-44.

Physiologic compensation mechanisms for hemorrhage include initial peripheral and mesenteric vasoconstriction to shunt blood to the central circulation. This is then augmented by a progressive tachycardia. Invasive monitoring may reveal an increased cardiac index, increased oxygen delivery (ie, $DO_2$), and increased oxygen consumption (ie, $VO_2$) by tissues. Lactate levels, the acid-base status, and other markers also may provide useful indicators of physiologic status. Age, medications, and comorbid factors all may affect a patient's response to hemorrhagic shock.

Failure of compensatory mechanisms in hemorrhagic shock can lead to death. Without intervention, a classic trimodal distribution of deaths is seen in severe hemorrhagic shock. An initial peak of mortality occurs within minutes of hemorrhage due to immediate exsanguination. Another peak occurs after 1 to several hours due to progressive decompensation. A third peak occurs days to weeks later due to sepsis and organ failure, which is a frequent consequence of reperfusion damage to the organs.

Treatment of shock caused by major blood loss is a great challenge, because secondary effects involving an inflammatory reaction and alterations in the coagulation system may have become independent and lead to the death of the patient irrespective of the question, whether adequate fluid and blood replacement has been possible. Specific treatment of major blood loss due to accidents or other wounds and of hemorrhagic shock consists of fluid resuscitation with crystalloids or colloids in order to reestablish organ perfusion. In addition, current procedures aim to relieve symptoms, which includes mechanical ventilation, fluid replacement, the use of cardio active drugs, strict control of oxygen saturation, hemoglobin, glucose and renal function. The control of the inflammation reaction only, e.g. with high dosage steroids or the inhibition of coagulation with anti thrombin, does not produce improvement of survival.

Shock as a sequel of blood loss and hemorrhagic shock is associated with overt or non-overt changes in plasma fibrinogen accompanied by fibrin formation and by an increase in fibrin fragments. This activation of clotting as well as fibrinolytic pathways may result in overt or non-overt disseminated intravascular coagulation (DIC) resulting in vessel occlusion and end-organ damage, and in consumption of coagulation factors resulting in bleeding. Importantly, fibrinogen, fibrin and fibrin fragments play not only a role in blood coagulation, but have several binding sites for cellular and matrix proteins, which allow them to interact with white blood cells, platelets, endothelial cells and matrix structures. This leads to cell activation, cell migration, cytokine release and ultimately to an inflammatory reaction. The role of fibrinogen or fibrin in inflammation is amply documented (reviewed by Altieri Thromb Haemost 82:781-786; Herrick et al. Int J Biochem Cell Biol 31:741-46). The D-region of the molecule contains many binding sites for matrix molecules, endothelial cells, platelets and inflammatory cells. The E-region of fibrin binds to CD11c (Loike et al. Proc Natl Acad Sci USA 88:1044-48).

We have recently described a novel role for the $Bbeta_{15-42}$ sequence of fibrin in inflammation (WO 02/48180). This sequence is also located within the E-region of fibrin and is only active when fibrinopeptide is cleaved. Fibrin fragments containing this sequence at their free N-terminus of the beta chain bind to endothelium and cause inflammation, and a peptide matching the aminoacids 15-42 of the Bbeta chain of fibrin blocks binding of fibrin fragments to endothelial surfaces and blocks inflammation in vitro (WO 02/48180). In vivo, this petide prevents myocardial inflammation and reduces myocardial infarct sizes in situations of ischemia/reperfusion (WO 02/48180).

Fibrin fragments occur in any situation of impaired fibrin formation and impaired fibrinolysis. Specifically in situations of shock this altered fibrin formation and fibrinolysis is a major problem. For many diseases a direct correlation between the outcome and the impairment of fibrin formation/fibrinolysis has been documented. E.g. Dengue (van Gorp et al. J Med Virol 2002, 67:549-54, Mairuhu et al. Lancet Inf Dis 2003; 3:33-41). Adult respiratory distress syndrome (ARDS) is a form of acute lung injury that is characterized by florid extravascular fibrin deposition (Idell Am J Respir Med. 2002; 1:383-91). Thrombosis in the pulmonary vasculature and disseminated intravascular coagulation have also been observed in association with ARDS.

SUMMARY OF THE INVENTION

The invention is concerned with the use of a peptide comprising the N-terminal sequence Gly-His-Arg-Pro-Leu-Asp-Lys-Lys-Arg-Glu-Glu-Ala-Pro-Ser-Leu-Arg-Pro-Ala-Pro--Pro-Pro-Ile-Ser-Gly-Gly-Gly-Tyr-Arg or any allelic variant or derivative of said peptide possessing the biological property of matching the inducible VE-cadherin binding motif on the Bβ-chain (i.e. $Bβ_{hd}$ 15-42) of human fibrin for the preparation of a pharmaceutical preparation for the treatment of shock.

In a preferred embodiment said peptide is

Gly-His-Arg-Pro-Leu-Asp-Lys-Lys-Arg-Glu-Glu-Ala-Pro-Ser-Leu-Arg-Pro-Ala-Pro--Pro-Pro-Ile-Ser-Gly-Gly-Gly-Tyr-Arg

We have found surprisingly that these peptides have a very beneficial effect in protecting warm-blooded animals from the consequences and complication of reperfusion after major bleeding events and of hemorrhagic shock. We were able to show that they are able to prevent the organ damage and organ failure which arise from acute inflammatory reactions caused by hemorrhagic shock and reperfusion. The peptides are able to prevent such diseases as Systemic Inflammatory Response Syndrom (SIRS), Acute Respiratory Distress Syndrome (ARDS), kidney failure, liver failure and multi-organ failure.

DETAILED DESCRIPTION OF THE INVENTION

Peptides and Proteins

Peptides were produced by solid-phase peptide synthesis and purified with reversed-phase HPLC using nucleosil 100-10C18 columns (PiChem, Graz, Austria). It should be noted that beta 15-42 region is 100% similar among species when allowing for conservative amino acid substitutions. The N-terminal disulfide knot of fibrinogen (NDSK) composed of amino-acids A$\alpha$1-51, B$\beta$1-118 and $\gamma$1-78 was prepared as previously described (WO 02/48180). The N-terminal disulfide knot of fibrin (NDSK-II, which lacks fibrinopeptides A and B) composed of aminoacids A$\alpha$17-51, B$\beta$15-118 and $\gamma$1-78 was prepared by treating NDSK with thrombin (20 U/1 mg of NDSK) for 3 h at 37° C. Residual thrombin was neutralized with 10 mM disopropyl fluorophosphate (Fluka, Milwaukee, Wis.) for 2 h at 37° C. All products were then dialyzed into phosphate buffered saline (PBS).

ELISA

Peptide B$\beta_{15-42}$ Binds to VE-Cadherin

The interaction of the Bbeta chain (Bbeta$_{15-42}$) of fibrin with endothelial cells causes morphologic changes (Bunce et al. J Clin Invest 89:842-50; Bach et al. Exp Cell Res 238:324-34; Chalupowicz et al. J Cell Biol 130:207-15; Hamaguchi et al. Blood 81:2348-56; Francis et al. Blood cells 19:291-306), proliferation (Sporn et al. Blood 86:1802-10), the release of von Willebrand factor (Ribes et al. J Clin Invest 79:117-23, Ribes et al. J Clin Invest 84: 435-42; Erban and Wagner, J Biol Chem 267, 2451-58;) and possibly IL-8 (Qi et al. Blood 90:3593-3602) and membrane expression of CD54 (Harley et al. Art Thromb Vasc Biol 20:652-658). VE-cadherin has been identified as a binding ligand of the sequence Bbeta$_{15-42}$ and ELISAs have been developed to demonstrate this interaction of endothelial cells and/or VE-cadherin with fibrin or fibrin fragments. Martinez et al. have used anti-pan cadherin antibodies to capture cadherins from endothelial cells followed by incubation with fibrin (Martinez et al. Ann NY Acad Sci 936:386-405), HUVEC monolayers (which express VE-cadherin) have been overlaid with radio-labeled fibrin fragments or peptide Bbeta$_{15-42}$ (Bach et al. J Biol Chem 273:30719-28; Harley et al. Art Thromb Vasc Biol 20:652-658), and recombinant VE-cadherin was used by Gorlatov and Medved (Biochemistry 41:4107-16). Others have used ELISA for detection of fibrin fragments within the blood, mostly by using antibodies to distinct sequences within the fibrinogen molecule including antibodies against the Bbeta$_{15-42}$ motif (reviewed in Fareed et al. Clin Chem 8:1845-53).

We have developed a modified ELISA working with the same principles described by others, but the purpose of the herein described ELISA is not to quantify fibrin degradation products, but to search for proteins, peptides or compounds which interfere with the binding of the Bbeta$_{15-42}$ sequence and the VE-cadherin. The principle is that the VE-cadherin, either as a truncated protein, as a full protein or coupled with other proteins which do not interfere with the Bbeta$_{15-42}$-binding site is allowed to interact with the Bbeta$_{15-42}$ sequence of fibrin. Into this system one can introduce any other additional substance and measure if this substance inhibits VE-cadherin/Bbeta$_{15-42}$ binding.

In detail, 96 well protein immobilizer plates (Exiqon, Vedbaek, DK) were coated with recombinant human VE-cadherin FC fusion protein (8 nM/ml; R&D Systems, Minneapolis) in PBS and were left overnight at 4° C. Plates were then washed and incubated with peptide B$\beta_{15-42}$ (GHRPLD-KKREEAPSLRPAPPPISGGGYR) tagged with a FLAG-sequence (DYKDDDDK) at the C-terminus of the peptide or with a FLAG-tagged random peptide (DRGAPAHRPPRG-PISGRSTPEKEKLLPG) at a concentration of 0-80 $\mu$Mol/ml. After washing, bound FLAG-tagged peptide was detected by incubation with a peroxidase-labelled anti-FLAG antibody (Sigma, St. Louis, USA) and chromogenic substrate. Optical density was determined by an ELISA plate reader set at a wavelength of 450 nm. Data represent the mean of three independent experiments, each performed in triplicates. The table below shows that the peptide B$\beta_{15-42}$ bound to VE-cadherin in a concentration-dependent manner. In contrast, the random peptide demonstrated only insignificant binding.

| Dose dependent binding of peptide Bbeta$_{15-42}$ to VE-cadherin | | | | | | | | | | |
|---|---|---|---|---|---|---|---|---|---|---|
| | | \u00b5M/ml | | | | | | | | |
| | | 0 | 0.23 | 0.7 | 2.3 | 7 | 14 | 21 | 35 | 46 | 70 |
| 15-42 | mean | 0 | 0.01 | 0.02 | 0.08 | 0.33 | 0.92 | 1.3 | 1.5 | 1.93 | 2.1 |
| FLAG | SD | 0 | 0.01 | 0.01 | 0.03 | 0.17 | 0.19 | 0.2 | 0 | 0 | 0 |
| random | mean | 0 | 0.01 | 0 | 0.01 | 0.03 | 0.12 | 0.2 | | 0.35 | 0.5 |
| FLAG | SD | 0 | 0.01 | 0 | 0.01 | 0.02 | 0.04 | 0.1 | | 0 | 0 |

Peptide B$\beta_{15-42}$ and fibrin fragments compete for binding to VE-cadherin.

In a next step, we analyzed whether this ELISA can be used to screen for other peptides/compounds to compete with the binding of the B$\beta_{15-42}$ sequence to VE-cadherin. As expected, peptide B$\beta_{15-42}$ completely inhibited binding of the flag-tagged peptide B$\beta_{15-42}$ and was used as the positive control and random peptides or solvent had no effect and were used as negative controls. Shorter peptides partially inhibited the binding of B$\beta_{15-42}$ to VE-cadherin. NDSK-II inhibited B$\beta_{15-42}$ binding in a concentration-dependent fashion. An equilibrium between B$\beta_{15-42}$ and NDSK-II (50% inhibition) was reached at a molar ratio of 24:1. NDSK had little or no effect.

VE-cadherin was coated to the plastic surface at a concentration of 8 nM/ml. Then indicated peptides were added at concentrations of 200 $\mu$M/ml, NDSK or NDSK-II were added at indicated concentrations. Detection of binding of the FLAG-tagged Bbeta$_{15-42}$ (12 μM/ml), was performed as described above.

In addition we have identified a specific assay for the determination of the claimed activity of the peptides, which consists of measurement of the inhibition of the release of interleukin-6 from endothelial cells. Interleukin-6 has been shown to be a strong predictor of the outcome and mortality in the situation of shock and is therefore a valuable parameter to determine the beneficial effects of the peptides. This assay is therefore also part of the invention.

| Blocking reagent | % inhibition of 15-42FLAG-binding to VE-cadherin mean ± SD |
| --- | --- |
| peptide 15-42 (28mer) | 100 ± 10 |
| peptide random (4mer) | 3 ± 3 |
| peptide random (28mer) | 10 ± 3 |
| solvent | 0 + 0 |
| peptide 15-18 (4mer) 200 μM/ml | 65 ± 12 |
| peptide 15-26 (12mer) 200 μM/ml | 64 ± 10 |
| peptide 15-30 (16mer) 200 μM/ml | 61 ± 13 |
| peptide 15-34 (20mer) 200 μM/ml | 67 ± 17 |
| peptide 15-37 (24mer) 200 μM/ml | 17 ± 19 |
| peptide 16-42 (27mer) 200 μM/ml | 55 ± 13 |
| peptide 15-18 (4mer) 12 μM/ml | 7 ± 2 |
| peptide 15-26 (12mer) 12 μM/ml | 6 ± 1 |
| peptide 15-30 (16mer) 12 μM/ml | 6 ± 3 |
| peptide 15-34 (20mer) 12 μM/ml | 7 ± 1 |
| peptide 15-37 (24mer) 12 μM/ml | 7 ± 2 |
| peptide 16-42 (27mer) 12 μM/ml | 5 ± 2 |
| NDSK-II 0.06 μM/ml | 1 + 0 |
| NDSK-II 0.12 μM/ml | 39 + 18 |
| NDSK-II 0.20 μM/ml | 42 + 14 |
| NDSK-II 0.60 μM/ml | 52 + 16 |
| NDSK-II 1.2 μM/ml | 63 + 13 |
| NDSK-II 2.4 μM/ml | 79 + 9 |
| NDSK-II 4.0 μM/ml | 82 + 12 |
| NDSK 0.06 μM/ml | 0 + 0 |
| NDSK 0.12 μM/ml | 2 + 1 |
| NDSK 0.20 μM/ml | 1 + 1 |
| NDSK 0.60 μM/ml | 7 + 6 |
| NDSK 1.2 μM/ml | 15 + 13 |
| NDSK 2.4 μM/ml | 16 + 9 |
| NDSK 4.0 μM/ml | 20 + 10 |
| anti-VE-cadherin Ab (TEA1/31, 1 mg/ml) | 2 + 1 |

Inhibition of the Release of Interleukin-6 from Endothelial Cells 96-well cell culture plates were coated with 1% gelatine. Into each well, approx. 23,000 human umbilical vein endothelial cells (HUVEC) in 200 μl of medium were pipetted. The HUVECs were taken from passage 4 form a pool of four different donors. The medium used for dilution was standard medium with 10% FCS, ECGS in *Iscove's modified Dulbecco medium* (Petzelbauer et al., J Immunol. 151:5062-5072, 1993). Within approx. 18 hrs at 37° C. in an incubator, a confluent cell monolayer is formed. The supernatant was removed and replaced with medium containing either NDSK-II alone or NDSK-II plus peptide Bβ$_{15A}$(GHRPLDKKREE-APSLRPAPPPISGGGYR).

The total final volume was 200 μl. After 4 hrs of incubation at 37° C. under 5% $CO_2$, the cell culture supernatant was again removed and centrifuged for 10 min at 4° C. at 3000 U/min. The concentration of interleukin-6 (IL-6) was measured using a commercial assay (IL-6 Quantikine Immonuassay (R&D Sytems; Catalog#: D6050; Lot: 231361). Calibration was done according to the standard protocol supplied by the assay manufacturer with various dilutions of recombinant IL-6 and medium. Readings of the optical density were taken at a wavelength of 450 nm with a reference wavelength of 550 nm.

| Results | |
| --- | --- |
| | IL-6 concentration in pg/ml |
| Medium | 12 ± 1 |
| 0.3 μg/ml NDSK-II | 19 ± 2 |
| 0.3 μg/ml NDSK-II + 10 μg/ml peptide | 15 ± 2 |
| 3 μg/ml NDSK-II | 25 ± 3 |
| 3 μg/ml NDSK-II + 10 μg/ml peptide | 12 ± 3 ($p < 0.05$ cmpd with NDSK-II alone) |
| 30 μg/ml NDSK-II | 21 ± 2 |
| 30 μg/ml NDSK-II + 10 μg/ml peptide | 13 ± 1 ($p < 0.05$ cmpd with NDSK-II alone) |

Hemorrhagic Shock in Domestic Pigs

Domestic male landrace pigs weighing 20-35 kg were fed a standard diet and received water ad libitum. All procedures were performed in concurrence with the AAALAC guidelines and according to the *Guide for the Care of Laboratory Animals* (Department of Health and Human Services, National Institutes of Health, Publication Nr. 86-23). Pigs were premedicated with azaperon (4 mg/kg). The ear vein was cannulated and the anesthetic propofol was applied. The animals were fully instrumented and equlibrated for 1 hr in order to recieve a stable baseline. Subsequently, the animals (n=16) were exsanguinated until a mean arterial pressure of 40 mm Hg was achieved. They were kept at this level constituting a hemorrhagic shock for 1 hr. After this time the lost blood volume was resubstituted with shed blood and salt solutions (cristalloids). In addition the animals received a bolus dose of the peptide Bβ15-42 (n=8) or a random sequence peptide (n=8) in a dose of 2.4 mh/kg each as a single intravenous bolus. During the ensuing reperfusion period over the duration of 5 hrs, Horrowitz index (measuring blood oxigenation), PEEP (positive end-expiratory pressure in mm Hg) and cardiac ejection volume were determined at various timepoints.

In the following tables the following timepoints were used:
Timepoint 1: 1 hr before hemorrhagic shock
Timepoint 2: during hemorrhagic shock
Timepoint 3: 1 hr after the start of reperfusion
Timepoint 4: 3 hrs after the start of reperfusion
Timepoint 5: 5 hrs after the start of reperfusion

| | Control Group | Treated Group | |
| --- | --- | --- | --- |
| | EV (ml) | | |
| 1: | 38 +/− 1 | 44 +/− 2 | |
| 2: | 6 +/− 1 | 6 +/− 1 | |
| 3: | 25 +/− 3 | 31 +/− 4 | $p < 0.05$ |
| 4: | 25 +/− 4 | 32 +/− 3 | $p < 0.05$ |
| 5: | 22 +/− 2 | 37 +/− 4 | $p < 0.05$ |
| | Horrowitz Index | | |
| 1: | 460 +/− 20 | 465 +/− 20 | |
| 2: | 395 +/− 60 | 450 +/− 20 | |
| 3: | 425 +/− 30 | 420 +/− 10 | |
| 4: | 360 +/− 50 | 410 +/− 20 | |
| 5: | 220 +/− 20 | 420 +/− 30 | $p < 0.05$ |
| | PEEP (mmHg) | | |
| 1: | 4 +/− 0.2 | 4 +/− 0.1 | |
| 2: | 4.3 +/− 0.3 | 4 +/− 0.1 | |
| 3: | 5 +/− 0.3 | 4.1 +/− 0.2 | $p < 0.05$ |
| 4: | 5.4 +/− 0.4 | 4.2 +/− 0.3 | $p < 0.05$ |
| 5: | 6.6 +/− 0.4 | 4.3 +/− 0.2 | $p < 0.05$ |

The invention claimed is:

1. A method for treating hemorrhagic shock comprising administering to an animal in need thereof a peptide comprising (SEQ ID NO: 1)
Gly-His-Arg-Pro-Leu-Asp-Lys-Lys-Arg-Glu-Glu-Ala- Pro-Ser-Leu-Arg-Pro-Ala-Pro-Pro-Pro-Ile-Ser-Gly- Gly-Gly-Tyr-Arg, wherein SEQ ID NO: 1 is the N-terminal sequence of said peptide and said peptide binds to VE-cadherin.

2. The method according to claim 1, characterized in that said peptide is

Gly-His-Arg-Pro-Leu-Asp-Lys-Lys-Arg-Glu-Glu-Ala-

Pro-Ser-Leu-Arg-Pro-Ala-Pro--Pro-Pro-Ile-Ser-Gly-

Gly-Gly-Tyr-Arg

3. The method according to claim 1, wherein shock is associated with Systemic Inflammatory Response Syndrome (SIRS), Acute Respiratory Distress Syndrome (ARDS), liver failure, kidney failure or multi-organ failure.

4. The method according to claim 2, wherein shock is associated with Systemic Inflammatory Response Syndrome (SIRS), Acute Respiratory Distress Syndrome (ARDS), liver failure, kidney failure or multi-organ failure.

* * * * *